United States Patent [19]

Carlisle et al.

[11] Patent Number: 5,437,824
[45] Date of Patent: Aug. 1, 1995

[54] METHOD OF FORMING A MOLDED SILICONE FOAM IMPLANT HAVING OPEN-CELLED INTERSTICES

[75] Inventors: Daniel A. Carlisle, Santa Barbara; Richard S. Waybright, Lompoc; Blanca Guillen, Goleta, all of Calif.

[73] Assignee: Moghan Medical Corp., Santa Barbara, Calif.

[21] Appl. No.: 172,851

[22] Filed: Dec. 23, 1993

[51] Int. Cl.⁶ .............................................. B29C 44/02
[52] U.S. Cl. ...................................... 264/50; 264/102
[58] Field of Search ................. 623/7, 8; 264/50, 46.6, 264/46.4, 51, 102

[56] References Cited

U.S. PATENT DOCUMENTS

| | | | |
|---|---|---|---|
| 3,919,724 | 11/1975 | Sanders et al. | 623/8 |
| 4,143,428 | 5/1979 | Cohen | 623/8 |
| 4,960,425 | 10/1990 | Yan et al. | 623/8 |
| 4,969,898 | 11/1990 | Calogero | 623/8 |
| 5,035,758 | 7/1991 | Degler et al. | 264/46.6 |
| 5,141,508 | 8/1992 | Bark et al. | 623/7 |
| 5,141,581 | 8/1992 | Markham | 264/46.4 |
| 5,171,269 | 12/1992 | Bark | 623/7 |

FOREIGN PATENT DOCUMENTS 2624725 6/1989 France .................... 623/8

*Primary Examiner*—Allan R. Kuhns
*Attorney, Agent, or Firm*—Michael G. Petit

[57] ABSTRACT

A breast prosthesis for implantation beneath the skin is disclosed. In one preferred embodiment the prosthesis has an outer elastic shell which encloses a biocompatible fluid and a silicone foam insert of unitary construction having the shape and approximate consistency of breast tissue. The foam insert occupies substantially the entire volume enclosed by the shell of the implantable prosthesis and consists of a foam body that is molded to the shape of the breast. The foam body has both open-cell and closed-cell characteristics. Portions of the foam insert are closed-cell with open-cell passageways threading themselves throughout the structure. The insert is of unitary construction and made by (a) heating a mold to an appropriate temperature; (b) mixing air bubbles into dispersion of uncured silicone; (c) injecting the bubble-laden, uncured silicone into the preheated mold; and (d) applying a vacuum until the foam insert cures. The volume of the foam insert should preferably be substantially equal to the unstretched volume of the shell which surrounds the foam body. In another preferred embodiment only a portion of the volume enclosed by the cell is occupied by the foam insert. In this embodiment, one surface of the foam insert conforms to the curvature of at least a portion of the shell and may be affixed to the conforming inner surface of the shell thereby effectively thickening or reinforcing the overlying shell. In yet another embodiment a foam insert made as described above comprising an open-cell and closed-cell foam body may directly implanted beneath the skin for breast augmentation or reconstruction without a shell. The inner surface of the mold may be textured to provide additional opportunity for desirable tissue ingrowth following implantation.

1 Claim, 3 Drawing Sheets

METHOD OF FORMING A MOLDED SILICONE FOAM IMPLANT HAVING OPEN-CELLED INTERSTICES

BACKGROUND OF THE INVENTION

1. Field of the Invention

This invention relates to a breast prosthesis for implantation beneath the skin, and more specifically, to the use of a foam body for such a prosthesis.

2. Definitions

The term "foam insert" as used herein means a unitary foam body having both open-cell and closed cell characteristics.

2. Description of the Prior Art

Breast implants are well known in the art. Silicone gel-filled implants useful for breast augmentation or reconstruction were introduced as early as 1963. Early embodiments provided a prosthesis with a peripheral seam, a thick shell, a heavy gel filling and a dacron patch on the posterior surface for affixing the implant onto the chest wall. Similar gel-filled implants have substantially dominated the reconstructive market until 1990.

There has been a renewed interest during the last 3 years in saline-filled breast implants. Saline has the advantage that in the event that the shell (which contains the saline) is ruptured, as for example due to a traumatic injury, the release of saline from the interior of the prosthesis is relatively safe to the person hosting the prosthesis. With this belief has come a resurgence in the development of saline-filled products. Notwithstanding the foregoing alleged advantage, saline-filled products have long been plagued with the problem of wrinkling which may occur when an elastic bag containing saline is anchored to the chest wall. When the patient is the upright position, the saline, being denser than the surrounding breast tissue travels under gravity towards the bottom of the envelope or shell and may cause wrinkling or creases to form in the superior portion, giving it an unnatural look. Moreover, "wave action", or "sloshing" of the saline within the implant occurs which is aesthetically undesirable. To overcome the potential problems of sloshing, wrinkling, and, in general, to improve the overall acceptability of a saline-filled implant, researchers have tried inserting various sorts of fillers into shells, which fillers, together with saline, provide a superior product that more closely resembles the density and hydrostatic properties of breast tissue. Thus, multilumen devices have been employed to provide a lubricious layer adjacent to the inner periphery of the shell and a second inner lumen containing saline therein. Others, such as U.S. Pat. 5,171,269 to Bark, describe inserting a fibrous material within the shell to impede the movement of saline in the interior volume of the shell and provide some structural integrity to the breast prosthesis. To date, none of the filler materials for saline implants have proven as natural feeling as the silicone gel-filled implants they are rapidly replacing.

SUMMARY OF THE INVENTION

It is an object of this invention to provide an insert for a fluid-filled breast prosthesis which gives the prosthesis a more natural appearance.

It is another object of this invention to provide an insert for a fluid-filled breast prosthesis, which insert, in conjunction with a fluid filler such as saline, provides a prosthesis which resists wrinkling regardless of the position of the wearer.

It is still another object of the invention to provide a saline-filled breast prosthesis with an insert material which is substantially non-toxic.

It is an object of this invention to provide a breast prosthesis comprising a unitary foam breast-shaped insert which may be implanted beneath the skin to augment or replace breast tissue without the need for a shell.

It is yet another object of the invention to provide a method for making a foam insert consisting of an open-celled and closed-celled unitary foam body suitable for implantation beneath the skin.

These and other objects of the invention will soon become apparent as we turn now to a brief description of the drawings and a description of the preferred embodiments.

DETAILED DESCRIPTION OF THE PREFERRED EMBODIMENTS

Figure 1:
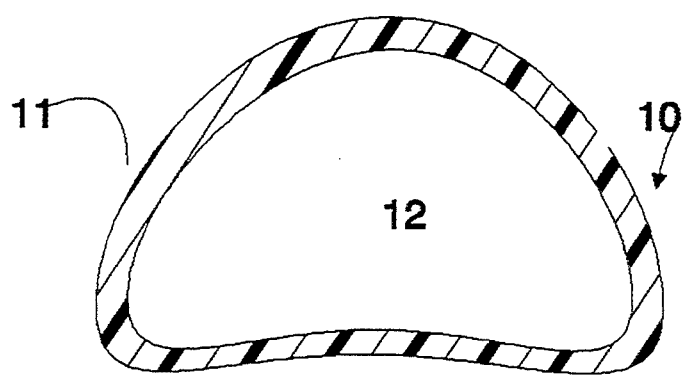
FIG. 1 shows a cross-sectional view of a prior art saline-filled implant.

In FIG. 1, we see a prior art breast prosthesis suitable for implantation beneath the skin, generally indicated at numeral 10. The prosthesis has an expandable outer shell 11 consisting of an elastic biocompatible material such as silicone. The shell 11 encases a fluid 12 such as saline or silicone gel. The problems with the saline-filled prosthesis have been described earlier under the Description of the Prior Art and need not be repeated here. Basically, the prior art saline-filled prostheses have an unnatural feel and the hydrostatic properties of the saline distort the shell when the wearer changes position.

Figure 2:
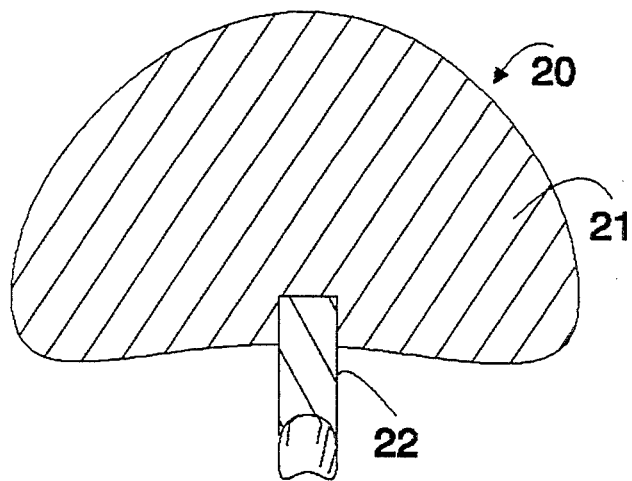
FIG. 2 is a cross sectional view of a mandrel used to form the outer shell of the prosthesis shown in FIG. 1.

Turning now to FIG. 2, we see a mandrel indicated at the numeral 20 which is used to cast a shell in accordance with the teachings of the prior art. The mandrel 20 comprises a substantially solid body portion 21 which has essentially the shape of the breast and a handle portion 22. The handle portion 22 is used to hold the mandrel 20 while repeatedly dipping the body portion 21 into a silicone dispersion (not shown) to form the shell 11. The shell is built up to its desired thickness by repeated dipping of the mandrel 20 into a silicone dispersion and curing before subsequent dips. After the final dip coat, the east shell is fully cured and stripped from the body portion 21 through a hole (not shown) cut around the handle portion 22.

Figure 3:
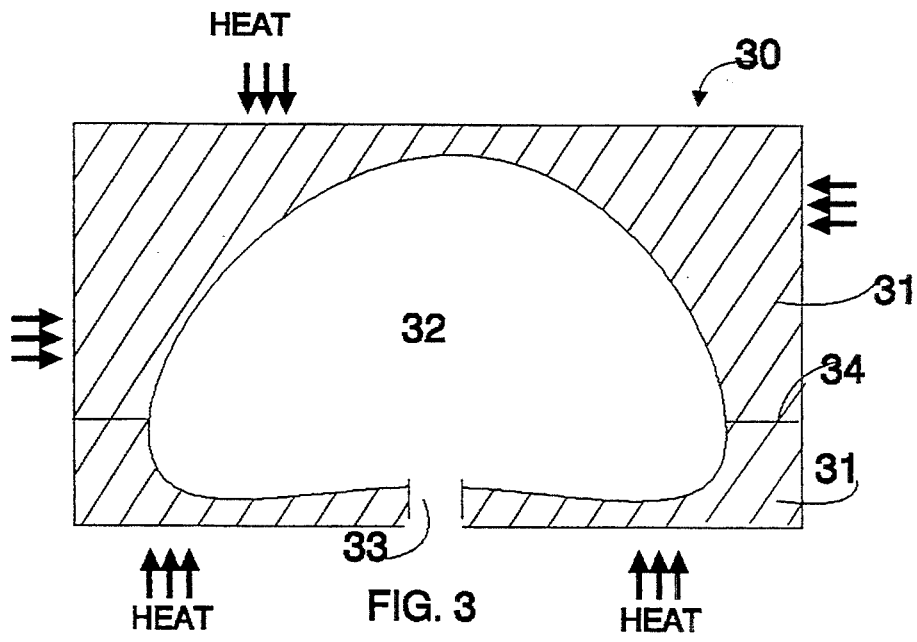
FIG. 3 is a cross sectional view of a single cavity mold made from the mandrel of FIG. 2.
Figure 4:
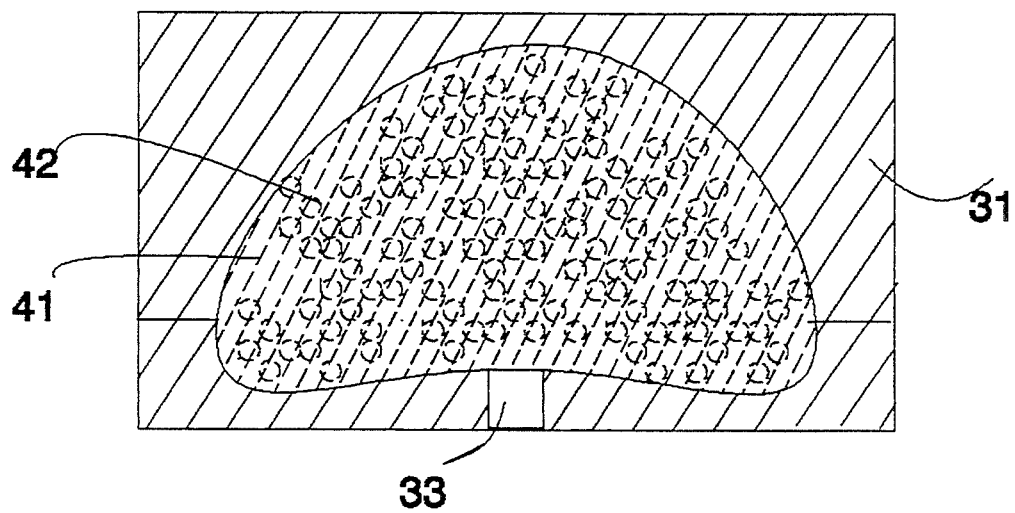
FIG. 4 is a cross sectional view showing bubble-filled, uncured silicone filling the mold cavity.
Figure 5:
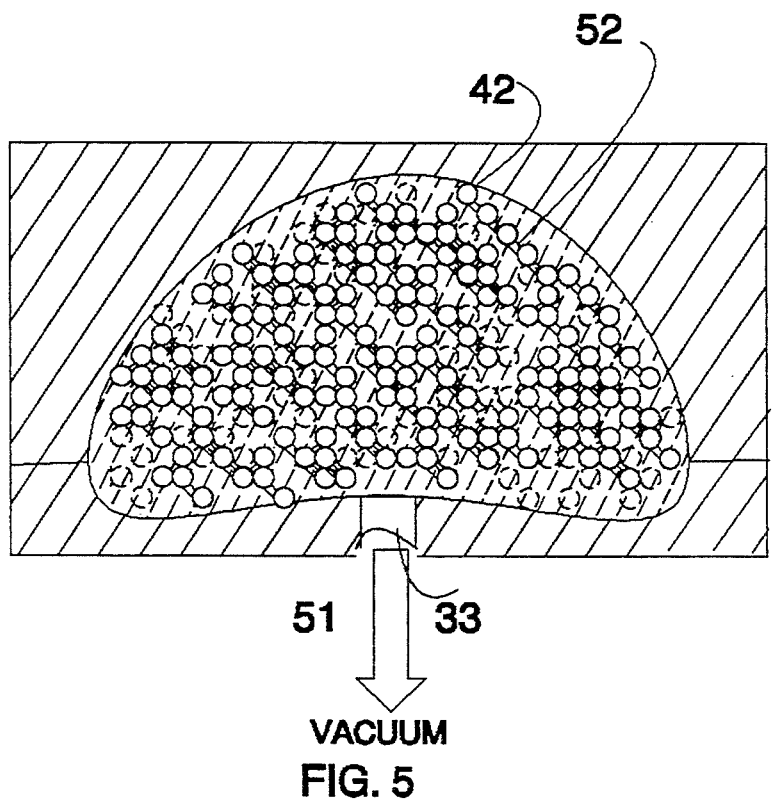
FIG. 5 is a cross sectional view of the mold of FIG. 4 showing the appearance of the foam when the vacuum is applied.
Figure 6:
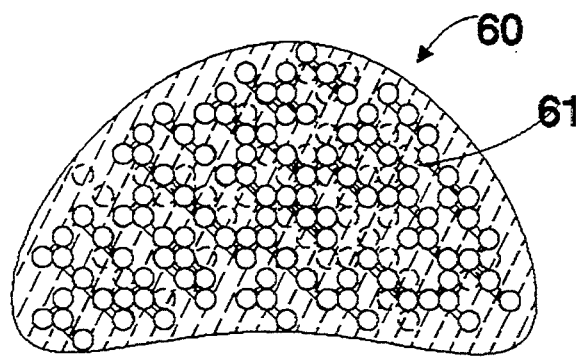
FIG. 6 shows the cross sectional view of a preferred embodiment of the present invention removed from the mold.

It is also possible to use the mandrel 20 for another purpose entirely. That is, the mandrel 20 may be used to produce a mold generally shown at 30 in FIG. 3 which mold 30 has a cavity 32 which is the same shape as the mandrel body 21. Thus, the mold cavity 32 is similar in size and encloses a volume similar to the shell 11. When making a foam insert in accordance with one preferred embodiment of the present invention the mold 30 is preheated to a temperature that will cure the outermost layer of silicone injected into the mold. In this regard, 350° F. is a satisfactory temperature. A silicone polymer, such as dimethylsiloxane with catalyst, is blended or rapidly stirred to introduce bubbles into the liquid elastomer and then injected into the cavity 32 of the preheated mold 30. After the aerated silicone dispersion is injected into the cavity 32 the mold 30 may be sealed with the exception of a vent 33 or vents that allow the aerated fluid silicone to escape from the cavity 32. The aerated liquid silicone elastomer 41 containing the bubbles 42 is shown in FIG. 4 filling the mold cavity 32. The vent(s) 33 in the mold 30 have a slight opening that will provide for silicone to overflow. The mold 30 is then placed in a vacuum chamber as shown in FIG. 5 until the silicone starts to flow out through the vent 33 in the mold. The vacuum (open arrow) is adjusted to keep the fluid silicone containing the bubbles in a static state thereby suspending the bubbles 42 within the closed mold. The mold filled with the fluid silicone/bubble suspension is maintained under a partial vacuum (20–30 inches of mercury) during the process of curing the material. Once the vacuuming and the partial or total curing is completed (usually about 60 minutes at 250° F. and 25 inches of mercury) the mold is removed from the vacuum chamber and opened along the parting seam 34. The silicone foam insert is ejected and any flash remaining thereon is removed. This molded insert 60 may then be placed in the outer shell 11 and a fluid such as saline added to fill the open-celled interstices in the foam insert. Alternatively, the foam insert 61 will be suspended in a biocompatible fluid such as saline until it is saturated, then placed within the shell 11 and a patch applied to seal the shell. The prosthesis is now ready for implantation.

Figure 7:
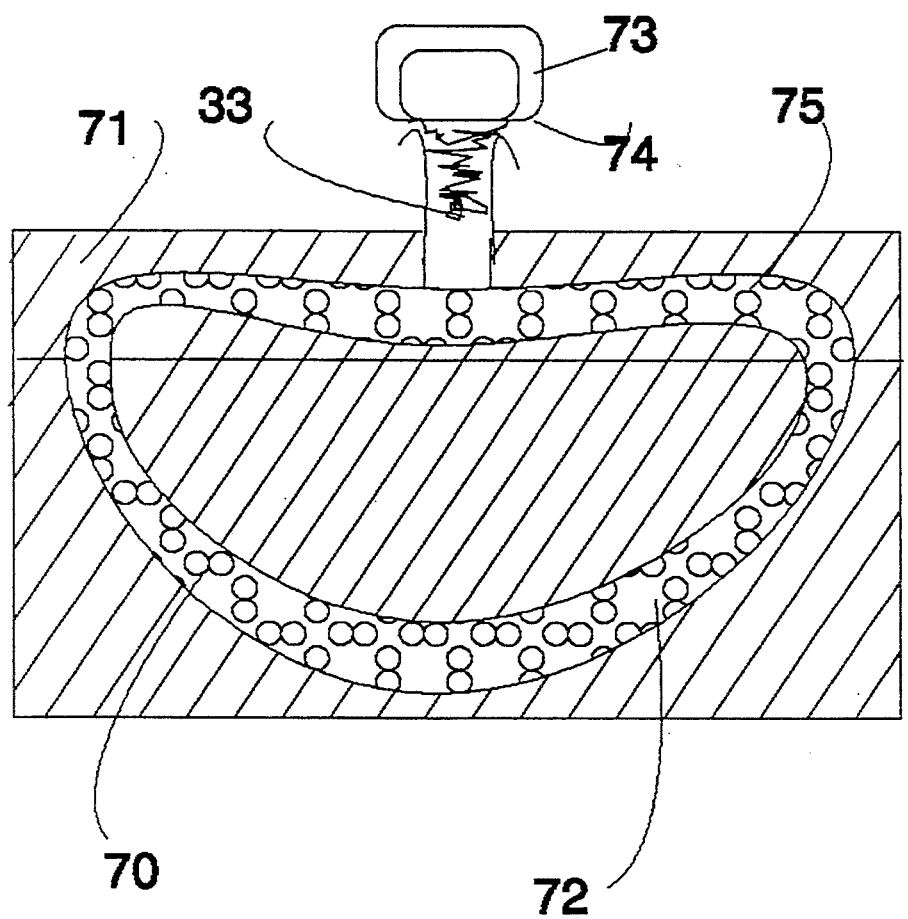
FIG. 7 is a cross sectional side view of a mold containing aerated fluid silicone in a cavity with another embodiment of the invention.
Figure 8:
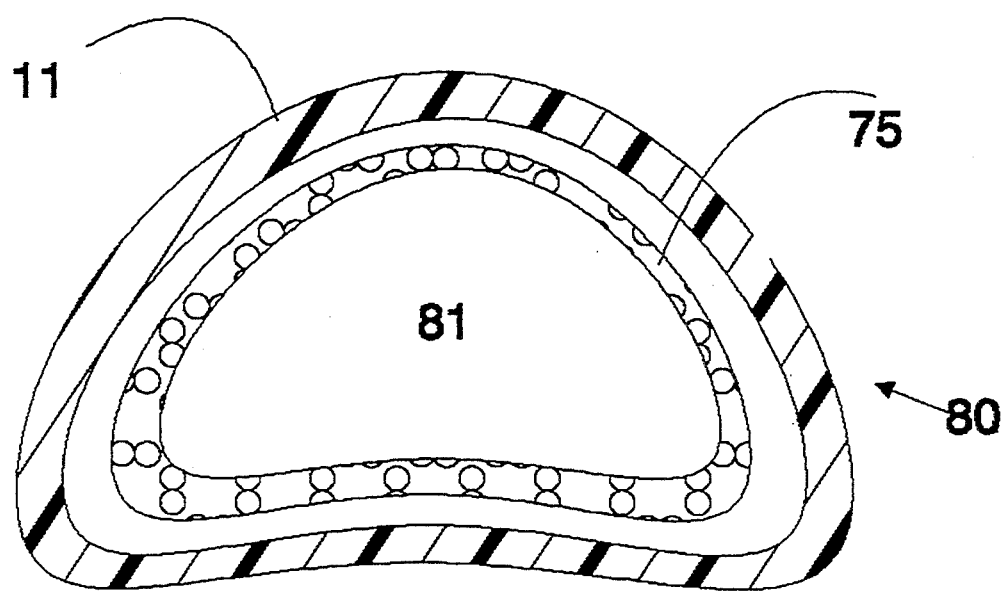
FIG. 8 is a cross sectional view of a breast prosthesis containing the foam insert of FIG. 7.

A different approach to improving the appearance and feel of a breast prosthesis, which is particularly useful for preventing wrinkling, also employs the foam insert of the present invention. FIG. 7 shows a mold 71 having a cavity 72 which has an outer surface 70 which anatomically conforms to at least a portion of the inner surface of a shell (not shown in FIG. 7). The mold 71 has a vent 33 as described earlier and may be fitted with a check valve as shown at 73 which comprises a cup with holes 74 at the bottom to prevent aerated silicone fluid ejected from the cavity during curing from returning to the cavity. After a medical grade silicone elastomer is injected into the mold cavity 72 and curing is complete, the foam insert 75 is ejected from the cavity 72 and may be either bonded to the inner surface of an elastomer shell 11 or left free-floating within the shell as shown in the prosthesis 80 of FIG. 8. The inner lumen 81 enclosed by the foam insert 75 can be filled by the introduction of a suitable fluid such as saline or silicone gel into the inner lumen 41 by valve means (not shown) well known in the art.

It is an inherent property of foam inserts, as defined herein, that they comprise a foam body having cells of both an open-celled and closed cell character. By varying the density of the closed cells in the (relatively dense) silicone, the density of the foam insert can be varied to closely approximate human breast tissue. This may be accomplished by varying the vacuum during the curing of the silicone foam body to create smaller or larger pores or bubbles therewithin. Foam inserts made according to the foregoing process are also suitable for implantation beneath the skin with or without a surrounding shell and/or saline.

EXAMPLE 1

A mold was preheated to 250° in an oven and poured with 140 grams of firm silicone and taped closed and sealed at the parting line. The mold was then exposed to a vacuum of 22 inches of mercury for 10 minutes. After 10 minutes, the vacuum was adjusted and set at 26–27 inches of mercury. The vacuum inside the chamber was not released. Approximately 40 grams of silicone material extruded or expanded through the mold opening at the top. Large bubbles were observed in the material escaping from the top of the mold. The mold was removed from the vacuum chamber after 30 minutes at 26–27 inches of mercury.

After the molded foam insert was removed from the mold, the foam insert was punched with an 11 mm square hole cutter making small to medium holes therethrough. The punched holes reduced the weight of the insert and created a sorer "feel" to the implant.

In summary then, a preferred embodiment of the invention provides a molded silicone foam insert that has both open and closed-cell characteristics. By first starting with a mold resembling the desired shape of the prosthesis, the fit between the outer shell and the molded silicone foam insert is exact. It might in some instances be preferable to make the silicone foam insert slightly undersized. That is, a mandrel may be used which is one or two sizes smaller than the mandrel used for dipping coating the shell. In this way, it can be assured that the shell will not be under tension; allowing for a more natural feel while still maintaining implant shape and reducing wrinkling. In another embodiment the foam insert is used without a shell for direct implantation beneath the skin. In still another embodiment a foam insert may be affixed to a portion of the inner surface of an elastomer outer shell to provide a prosthesis having a more natural appearance. made without departing from the spirit and scope of the invention. It is therefore intended to cover in the appended claims all such changes and modifications that are within the scope of this invention.

What I claim is:

1. A method for making a foam insert for use with a saline filled breast implant comprising the steps of:
   (a) creating gaseous bubbles within a fluid silicone;
   (b) preheating a mold to 200° to 300° F.;
   (c) injecting said fluid silicone containing said bubbles into a cavity within the preheated mold;
   (d) reducing the external pressure exerted on said fluid silicone within said cavity of said mold below atmospheric pressure;
   (e) curing said fluid silicone by holding the mold at elevated temperature and reduced pressure for 30 to 60 minutes to form a foam insert; and
   (f) removing said foam insert from said cavity in said mold, wherein the reduced pressure operates to force a portion of said bubbles from said fluid silicone while said fluid silicone is curing to form said foam insert having open-celled interstices.

* * * * *

UNITED STATES PATENT AND TRADEMARK OFFICE
CERTIFICATE OF CORRECTION

PATENT NO. : 5,437,824
DATED : August 1, 1995
INVENTOR(S) : Daniel A. Carlisle, Richard S. Waybright and Blanca Guillen It is certified that error appears in the above-indentified patent and that said Letters Patent is hereby corrected as shown below:

On the title page: Item [73]
Assignee should read --McGhan Medical Corp.--

Signed and Sealed this

Ninth Day of December, 1997

Attest:

BRUCE LEHMAN

Attesting Officer

Commissioner of Patents and Trademarks